(12) United States Patent
Markosyan

(10) Patent No.: US 8,735,101 B2
(45) Date of Patent: *May 27, 2014

(54) GLUCOSYL STEVIA COMPOSITION

(75) Inventor: Avetik Markosyan, Yerevan (AM)

(73) Assignee: PureCircle USA Inc., Oak Brook, IL (US)

( * ) Notice: Subject to any disclaimer, the term of this patent is extended or adjusted under 35 U.S.C. 154(b) by 0 days.

This patent is subject to a terminal disclaimer.

(21) Appl. No.: 13/589,754

(22) Filed: Aug. 20, 2012

(65) Prior Publication Data

US 2012/0315355 A1   Dec. 13, 2012

Related U.S. Application Data

(63) Continuation of application No. 13/074,179, filed on Mar. 29, 2011, now Pat. No. 8,318,459, which is a continuation-in-part of application No. 13/029,263, filed on Feb. 17, 2011, now Pat. No. 8,257,948.

(51) Int. Cl.
| | |
|---|---|
| *A23L 1/236* | (2006.01) |
| *C12P 15/00* | (2006.01) |
| *C12P 7/62* | (2006.01) |
| *C12P 7/02* | (2006.01) |
| *C12P 19/56* | (2006.01) |

(52) U.S. Cl.
USPC ............. 435/78; 435/127; 435/135; 435/155; 426/548

(58) Field of Classification Search
CPC ...... A23L 1/236; A23L 1/2365; A23L 1/2363; C12P 7/02; C12P 7/62; C12P 19/56
See application file for complete search history.

(56) References Cited

U.S. PATENT DOCUMENTS

| | | | |
|---|---|---|---|
| 8,257,948 B1 * | 9/2012 | Markosyan | 435/78 |
| 8,318,459 B2 * | 11/2012 | Markosyan | 435/78 |
| 2009/0053378 A1 * | 2/2009 | Prakash et al. | 426/548 |

* cited by examiner

*Primary Examiner* — Blaine Lankford
*Assistant Examiner* — Charles Zoltan Constantine
(74) *Attorney, Agent, or Firm* — Briggs and Morgan, P.A.; Aleya R. Champlin

(57) ABSTRACT

Glucosyl stevia compositions are prepared from steviol glycosides of *Stevia rebaudiana* Bertoni. The glucosylation was performed by cyclodextrin glucanotransferase using the starch as source of glucose residues. The short-chain glucosyl stevia compositions were purified to >95% content of total steviol glycosides. The compositions can be used as sweetness enhancers, flavor enhancers and sweeteners in foods, beverages, cosmetics and pharmaceuticals.

21 Claims, 3 Drawing Sheets

GLUCOSYL STEVIA COMPOSITION

RELATED APPLICATIONS

This application is a continuation application of, and claims the benefit of priority from, U.S. patent application Ser. No. 13/074,179, filed on Mar. 29, 2011, now U.S. Pat. No. 8,318,459 which is a continuation-in-part application of, and claims the benefit of priority from, U.S. patent application Ser. No. 13/029,263, filed on Feb. 17, 2011 now U.S. Pat. No. 8,257,948.

BACKGROUND OF THE INVENTION

1. Field of the Invention

The invention relates to a process for producing a highly purified food ingredient from the extract of the *Stevia rebaudiana* Bertoni plant and its use in various food products and beverages.

2. Description of the Related Art

Nowadays sugar alternatives are receiving increasing attention due to awareness of many diseases in conjunction with consumption of high-sugar foods and beverages. However many artificial sweeteners such as dulcin, sodium cyclamate and saccharin were banned or restricted in some countries due to concerns on their safety. Therefore non-caloric sweeteners of natural origin are becoming increasingly popular. The sweet herb *Stevia rebaudiana* Bertoni, produces a number of diterpene glycosides which feature high intensity sweetness and sensory properties superior to those of many other high potency sweeteners.

The above-mentioned sweet glycosides, have a common aglycon, steviol, and differ by the number and type of carbohydrate residues at the C13 and C19 positions. The leaves of *Stevia* are able to accumulate up to 10-20% (on dry weight basis) steviol glycosides. The major glycosides found in *Stevia* leaves are Rebaudioside A (2-10%), Stevioside (2-10%), and Rebaudioside C (1-2%). Other glycosides such as Rebaudioside B, D, E, and F, Steviolbioside and Rubusoside are found at much lower levels (approx. 0-0.2%).

Two major glycosides—Stevioside and Rebaudioside A, were extensively studied and characterized in terms of their suitability as commercial high intensity sweeteners. Stability studies in carbonated beverages confirmed their heat and pH stability (Chang S. S., Cook, J. M. (1983) Stability studies of stevioside and Rebaudioside A in carbonated beverages. *J. Agric. Food Chem.* 31: 409-412.)

Steviol glycosides differ from each other not only by molecular structure, but also by their taste properties. Usually stevioside is found to be 110-270 times sweeter than sucrose, Rebaudioside A between 150 and 320 times, and Rebaudioside C between 40-60 times sweeter than sucrose. Dulcoside A is 30 times sweeter than sucrose. Rebaudioside A has the least astringent, the least bitter, and the least persistent aftertaste thus possessing the most favorable sensory attributes in major steviol glycosides (Tanaka O. (1987) Improvement of taste of natural sweetners. *Pure Appl. Chem.* 69:675-683; Phillips K. C. (1989) *Stevia*: steps in developing a new sweetener. In: Grenby T. H. ed. Developments in sweeteners, vol. 3. Elsevier Applied Science, London. 1-43.)

Methods for the extraction and purification of sweet glycosides from the *Stevia rebaudiana* plant using water or organic solvents are described in, for example, U.S. Pat. Nos. 4,361,697; 4,082,858; 4,892,938; 5,972,120; 5,962,678; 7,838,044 and 7,862,845.

However, even in a highly purified state, steviol glycosides still possess undesirable taste attributes such as bitterness, sweet aftertaste, licorice flavor, etc. One of the main obstacles for the successful commercialization of stevia sweeteners are these undesirable taste attributes. It was shown that these flavor notes become more prominent as the concentration of steviol glycosides increases (Prakash I., DuBois G. E., Clos J. F., Wilkens K. L., Fosdick L. E. (2008) Development of rebiana, a natural, non-caloric sweetener. Food Chem. Toxicol., 46, S75-S82.)

Some of these undesirable properties can be reduced or eliminated by subjecting steviol glycosides to the reaction of intermolecular transglycosylation, when new carbohydrate residues are attached to initial molecule at C13 and C19 positions. Depending on the number of carbohydrate residues in these positions the quality and potency of the compounds taste will vary.

Pullulanase, isomaltase (Lobov S. V., Jasai R., Ohtani K., Tanaka O. Yamasaki K. (1991) Enzymatic production of sweet stevioside derivatives: transglycosylation by glucosidases. *Agric. Biol. Chem.* 55: 2959-2965), β-galactosidase (Kitahata S., Ishikawa S., Miyata T., Tanaka O. (1989) Production of rubusoside derivatives by transglycosylation of various β-galactosidase. *Agric. Biol. Cheng.* 53: 2923-2928), and dextran saccharase (Yamamoto K., Yoshikawa K., Okada S. (1994) Effective production of glucosyl-stevioside by α-1,6-transglucosylation of dextran dextranase. *Biosci. Biotech. Biochem.* 58: 1657-1661) have been used as transglycosylating enzymes, together with pullulan, maltose, lactose, and partially hydrolyzed starch, respectively, as donors of glycosidic residues.

The transglucosylation of steviol glycosides was also performed by action of cyclodextrin glucanotransferases (CG-Tase) produced by *Bacillus stearothermophilus* (U.S. Pat. Nos. 4,219,571, and 7,807,206) as a result α-1,4-glucosyl derivatives were formed with degree of polymerization up to 10.

It was shown that the taste profile and sweetness power of glucosyl derivatives are largely dependent on number of additional glucosyl derivatives, i.e. the degree of polymerization of the α-1,4-glucosyl chain. The increase in number of α-1, 4-glucosyl residues improved the taste quality but at the same time reduced the sweetness level. The treatment of transglucosylated stevioside with β-amylase resulted in a product consisting of mono- or di-α-1,4-glucosyl derivatives with better taste profile and optimal sweetness level (Tanaka, 1987). However in such process, the resulting product contains high level of initial unreacted (unmodified) glycosides (generally >20%) which makes it not compliant with regulatory requirements of less than 15% unreacted glycosides (α-Glucosyltransferase Treated *Stevia*, *Japan's Specifications and Standards for Food Additives*, VIII edition, 2009, p. 257). Therefore additional steps for chromatographic separation of unreacted steviol glycosides are used to reduce initial unreacted (unmodified) glycosides' content. However chromatographic separation techniques generally involve high cost and are not suitable for large scale production.

It is to be noted also that many glucosyl stevia products contain up to 20% residual dextrins which do not possess significant functional properties and reduce the content of steviol glycosides in the product.

Therefore it is necessary to develop simple process of preparation of high purity glucosyl stevia products with optimal α-1,4-glucosyl chain length and low unreacted glycosides level.

SUMMARY OF THE INVENTION

The present invention is aimed to overcome the disadvantages of existing *Stevia* sweeteners. The invention describes a process for producing a high purity food ingredient from the extract of the *Stevia rebaudiana* Bertoni plant and use thereof in various food products and beverages as a sweetness and flavor modifier.

The invention, in part, pertains to an ingredient comprising glucosylated derivatives of steviol glycosides of *Stevia rebaudiana* Bertoni plant. The steviol glycodsides are selected from the group consisting of stevioside, Rebaudioside A, Rebaudioside B, Rebaudioside C, Rebaudioside D, Rebaudioside E, Rebaudioside F, dulcoside A, steviolbioside, rubusoside, as well as other steviol glycosides found in *Stevia rebaudiana* Bertoni plant and mixtures thereof.

The invention, in part, pertains to a process for producing an ingredient containing glucosylated forms of stevioside, Rebaudioside A, Rebaudioside B, Rebaudioside C, Rebaudioside D, Rebaudioside E, Rebaudioside F, dulcoside A, steviolbioside, rubusoside, as well as other steviol glycosides found in *Stevia rebaudiana* Bertoni plant. The process can be an enzymatic transglucosylating process using CGTases produced by cultures of *Bacillus stearothermophilus*. The process may include the step of shortening glucosyl chains by $\beta$-amylase. The process can also have the steps of decolorizing, desalting and removing maltooligosaccharides and unmodified (unreacted) steviol glycosides. The decolorizing can be performed using activated carbon. The desalting can be performed by passing through ion exchange resins and/or membrane filters. Removing the maltooligosaccharides can be performed by passing through macroporuos polymeric resin. Removing unmodified (unreacted) steviol glycosides can be performed by suspending the product in aqueous alcohol.

In the invention, *Stevia* extract commercialized by PureCircle (JiangXi) Co., Ltd. (China), containing stevioside (28-30%), Rebaudioside A (50-55%), Rebaudioside C (9-12%), Rebaudioside F (1-3%) and other glycosides amounting to total steviol glycosides' content of at least 95%, was used as a starting material. Alternatively stevia extracts with different ratio of steviol glycosides as well as highly purified steviol glycosides such as Rebaudioside A, stevioside, Rebaudioside D, rubusoside etc, may be used as starting materials.

The starting material was subjected to the enzymatic transglucosylation by action of cyclodextrin glycosyltransferase (CGTase) in the presence of starch as a glucose donor. As a result $\alpha$-1,4-glucosyl derivatives were formed with degree of polymerization up to 10. Then the formed derivatives were subjected to treatment with $\beta$-amylase to produce $\alpha$-1,4-glucosyl derivatives possessing a degree of polymerization up to 2.

The oligosaccharides from obtained reaction mixture were removed by Amberlite XAD7 HP resin, and then decolorized, deionized, concentrated and spray dried.

The unreacted steviol glycosides were subsequently removed by suspending the dried product in organic solvent and separating the suspended solids containing decreased level of unreacted steviol glycosides.

The obtained products were applied in various foods and beverages as sweeteners, sweetener enhancers and flavor modifiers, including ice cream, cookies, bread, fruit juices, milk products, baked goods and confectionary products.

It is to be understood that both the foregoing general description and the following detailed description are exemplary and explanatory and are intended to provide further explanation of the invention as claimed.

BRIEF DESCRIPTION OF THE DRAWINGS

The accompanying drawings are included to provide a further understanding of the invention. The drawings illustrate embodiments of the invention and together with the description serve to explain the principles of the embodiments of the invention.

DETAILED DESCRIPTION OF THE INVENTION

Figure 1:
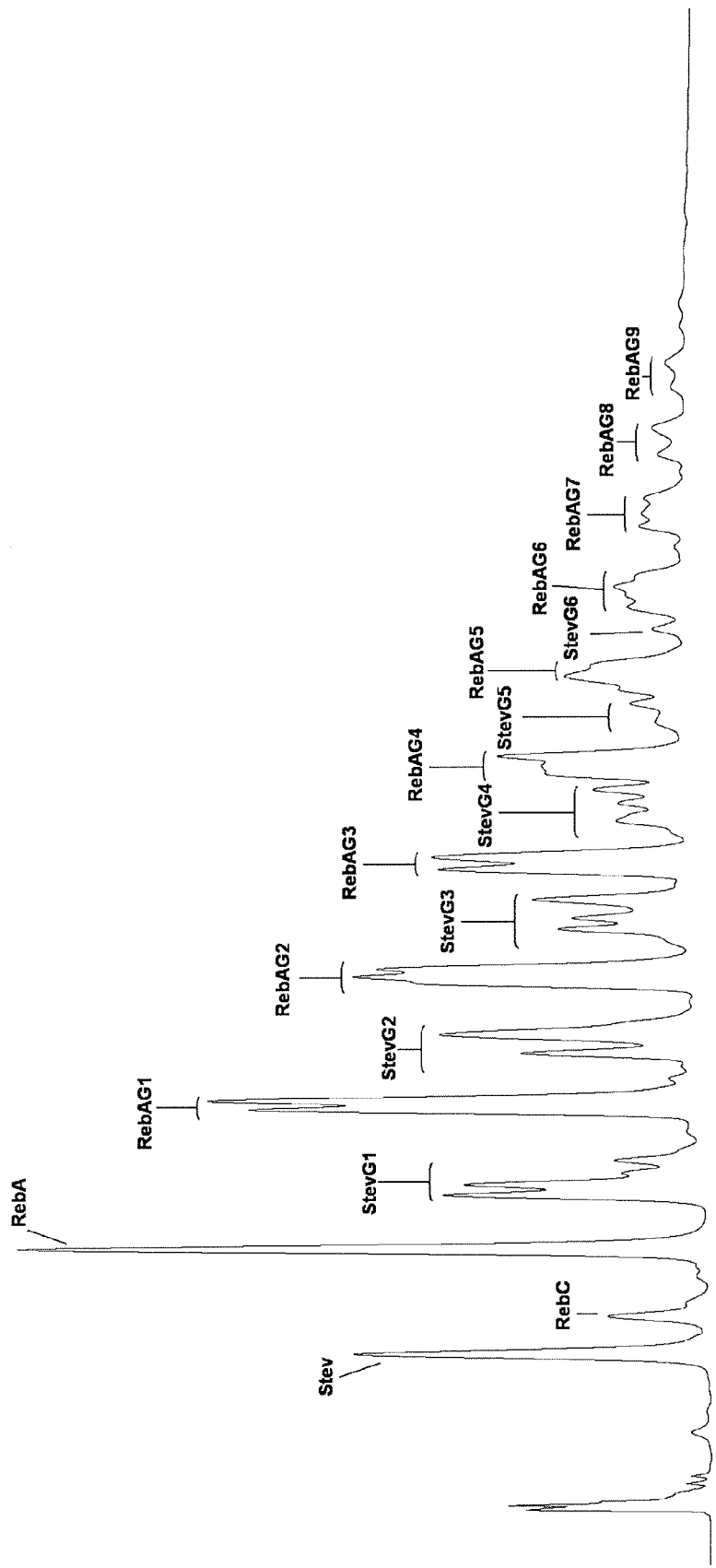
FIG. 1 shows a high-performance liquid chromatographic chromatogram of purified transglucosylated *Stevia* extract without $\beta$-amylase treatment containing long-chain $\alpha$-1,4-glucosyl-derivatives with up to nine $\alpha$-1,4-glucosyl residues.
Figure 2:
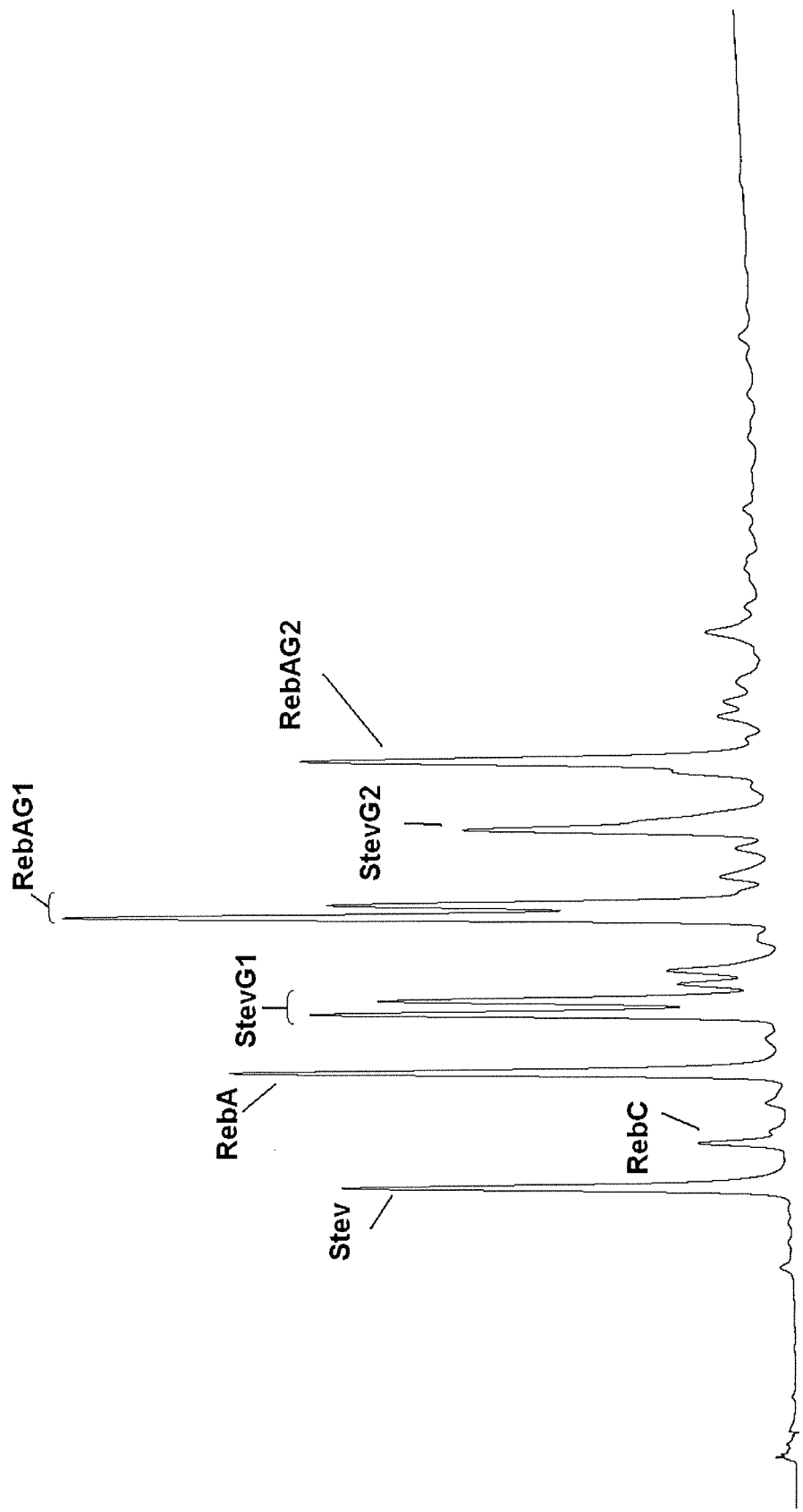
FIG. 2 shows a high-performance liquid chromatographic (HPLC) chart of $\beta$-amylase treated product containing mono- and di-$\alpha$-1,4-glucosyl-derivatives of steviol glycosides, as well as high level of unreacted steviol glycoside.
Figure 3:
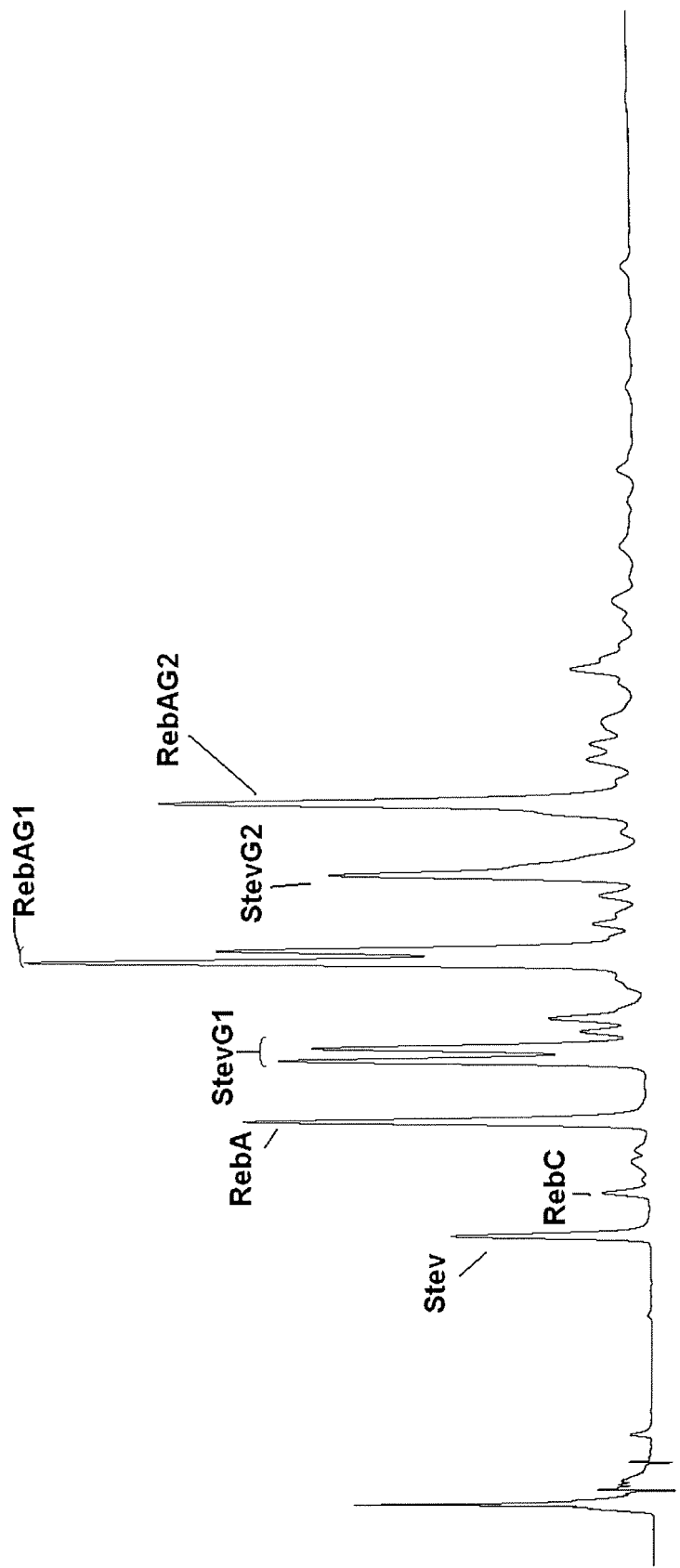
FIG. 3 shows a high-performance liquid chromatographic (HPLC) chart of $\beta$-amylase treated product containing mono- and di-$\alpha$-1,4-glucosyl-derivatives of steviol glycosides, as well as low level of unreacted steviol glycosides.

Advantages of the present invention will become more apparent from the detailed description given hereinafter. However, it should be understood that the detailed description and specific examples, while indicating preferred embodiments of the invention, are given by way of illustration only, since various changes and modifications within the spirit and scope of the invention will become apparent to those skilled in the art from this detailed description.

*Stevia* extract commercialized by PureCircle (JiangXi) Co., Ltd. (China), containing stevioside (28-30%), Rebaudioside A (50-55%), Rebaudioside C (9-12%), Rebaudioside F (1-3%) and other glycosides (hereinafter collectively, "steviol glycosides") amounting to total steviol glycosides content of at least 95%, was used as a starting material. Alternatively stevia extracts with different ratio of steviol glycosides as well as highly purified steviol glycosides such as Rebaudioside A, stevioside, Rebaudioside D, rubusoside etc, may be used as starting materials.

The HPLC analysis of the raw materials and products was performed on Agilent Technologies 1200 Series (USA) liquid chromarograph, equipped with Zorbax-NH$_2$ (4.6×250 mm) column. The mobile phase was acetonitrile-water gradient from 80:20, v/v (0-2 min) to 50:50, v/v (2-70 min). A diode array detector set at 210 nm was used as the detector.

The transglucosylation was accomplished by cyclomaltodextrin glucanotransferases (CGTases; EC 2.4.1.19) produced by *Bacillus stearothermophilus* St-100 (PureCircle Sdn Bhd Collection of Industrial Microorganisms—Malaysia). However, any other CGTase or enzyme possessing intermolecular transglucosylation activity may be applied as well. The enzyme can be in a form of cell-free culture broth, concentrated liquid cell-free culture broth, spray dried or freeze dried cell-free culture broth, or high purity protein. Free and immobilized enzyme preparations can be used.

The activity of CGTase preparations was determined according to the procedure described in Hale W. S., Rawlins L. C. (1951) Amylase of *Bacillus macerans*. Cereal Chem. 28, 49-58.

Starches of different origin may be used as donors of glucosyl units such as, derived from wheat, corn, potato, tapioca, and sago.

Starch was subjected to partial hydrolysis (liquefaction) prior to the transglycosylation reaction. The dextrose equivalent of the partially hydrolyzed starch can be in the range of about 10-25, preferably about 12-16. Any enzyme capable of starch hydrolysis may be used for liquefaction, such as α-amylases, β-amylases etc. In one embodiment, CGTase and α-amylase mixtures as liquefying enzymes are preferred.

α-Amylase activity is expressed in Kilo Novo α-amylase Units (KNU). One KNU is the amount of α-amylase which, under standard conditions (pH 7.1; 37° C.), dextrinizes 5.26 g starch dry substance per hour.

The liquefaction mixture contains about 0.001-0.2 KNU, preferably about 0.05-0.1 KNU of α-amylase per one unit of CGTase.

The use of α-amylase in liquefaction allows achieving higher throughputs in further activated carbon filtration. When the CGTase is used as the only liquefying enzyme the filtration rate is approximately 10-15 L/hr per 1 $m^2$ of filter surface. In case of liquefaction enzyme mixture (comprising α-amylase and CGTase) the filtration rate is twice as fast—approximately 20-30 L/hr per 1 $m^2$ of filter surface.

The ratio of starch and CGTase in the liquefaction mixture is about 0.1-0.5 units per one gram of starch, preferably about 0.2-0.4 units per gram.

The concentration of starch in liquefaction mixture is about 15-40% (wt/wt), preferably about 20-30%.

The liquefaction is conducted at about 70-90° C. during about 0.5-5 hours, preferably about 1-2 hours.

After liquefaction, the reaction mixture is subjected to thermal inactivation of α-amylase at low pH conditions. The preferred pH range for inactivation is about pH 2.5 to pH 3.0 and preferred temperature is about 95-105° C. The duration of thermal inactivation is about 5-10 minutes.

After the inactivation, the pH of the reaction mixture is adjusted to about pH 5.5-6.5 and the steviol glycosides are added to the mixture and dissolved. The preferred ratio of steviol glycosides to starch (kg of steviol glycosides per 1 kg of starch) is about 0.5-1.5, preferably about 0.8-1.2.

A second portion of CGTase preparation is added and the transglucosylation reaction is conducted at about 65° C. for about 24-48 hours. The amount of the second portion of CGTase is about 0.2-4 units of CGTase per gram of solids, preferably about 0.5-1.2 units per gram of solids.

Upon completion of transglucosylation reaction, about 30-50 units per gram of solids of β-amylase was added and the reaction was continued for about 12-16 hours at about 35-55° C., preferably about 45° C. β-Amylase produced by *Bacillus polymyxa* St-3504 (PureCircle Sdn Bhd Collection of Industrial Microorganisms—Malaysia) was used in this stage. However β-amylases, and other starch hydrolyzing enzymes derived from any other source including soybean, barley, bacterial, fungal and others may be used as well.

β-Amylase activity unit (1 AUN) is defined as the activity which liberates 100 μg of reducing sugar (expressed by dextrose equivalent) per minute under the following conditions: 1 mL of enzyme solution is mixed with 5 mL of 1.2% starch solution (pH 5.5, M/20 Acetate Buffer) and kept for 20 min at 40° C.

The reaction was stopped by heating at about 95° C. for about 15 minutes to inactivate the enzymes, and the solution was treated with activated carbon, to obtain decolorized reaction mixture. The amount of activated carbon was about 0.02-0.4 grams per gram of solids, preferably about 0.05-0.2 grams per gram of solids.

The decolorized reaction mixture was desalted by passing through ion exchange resins, such as Amberlite FPC23 ($H^+$ type) and Amberlite FPA51 ($OH^-$ type). Other appropriate decolorizing and desalting methods, such as membrane filtration, or other methods known in the art can be used.

The desalted reaction mixture was further concentrated by vacuum evaporator and dried by means of a spray dryer. Other appropriate concentrating and drying methods, such as membrane filtration, freeze drying, or other methods known to art can be used.

The dried powder was suspended in aqueous alcohol. The powder to aqueous alcohol ratio (wt/vol) was 1:1 to 1:20, preferably 1:3 to 1:10. The aqueous alcohol contained 0-50% (vol), preferably 1-10% water. The suspension is agitated at 30-100° C., preferably 50-85° C. during 1-24 hours, preferably 2-15 hours. Then the suspended solids are separated by means of filtration. Any other technique known in the art suitable for separating suspended solids from liquid such as centrifugation, decanting, etc. can be used. The obtained solids are dried in rotary drum vacuum drier. Any other dryer known t in the art may be used as well. Alternatively the separated solids may be dissolved in water, evaporated from traces of alcohol and spray dried.

The alcohols employed in the invention may be selected from the group consisting of alkanols, and are preferably selected from the group including methanol, ethanol, n-propanol, 2-propanol, 1-butanol, and 2-butanol.

The resulting product contains low level non-modified glycosides, short-chain (containing two or less α-1,4-glucosyl residues) derivatives and a mixture of maltooligosaccharides (Sample 1). As used herein, the expressions "low level non-modified glycosides" or "low level unreacted glycosides" shall refer to glycoside levels of less than about 20%, and preferably less than about 15%, on an anhydrous basis. In some embodiments, an unreacted glycoside level of about 12%, about 10% or even lower can be attained using this method.

In order to prepare a product with higher content of total sweet glycosides (the sum of glycosylated and non-glycosylated glycosides), the maltooligosaccharides were removed using Amberlite XAD7 HP prior to the desalting treatment. The steviol glycosides and their glucosylated derivatives were adsorbed on the resin and subsequently eluted by aqueous ethanol. The resulted aqueous ethanol eluate, containing glucosyl steviol glycosides, was subsequently decolorized and desalted as described above and the glycosides solution, after the evaporation of eluting solvent, was powdered by spray drying. The dried powder was suspended in aqueous alcohol and processed as described above to remove unmodified (unreacted) steviol glycosides. The resulting product contains low level non-modified glycosides, and short-chain (containing two or less α-1,4-glucosyl residues) derivatives (Sample 2).

The embodiments of the invention exemplified by Samples 1 and 2 are free or substantially free of higher glucosylated derivatives having more than 2 glucosyl residues. In accordance with this invention, the highly purified glucosyl stevia composition preferably comprises greater than about 50% by weight mono-, and diglucosyl steviol glycosides.

Using a similar process as for Sample 2, with exclusion of the β-amylase and aqueous alcohol treatment stages, a product containing non-modified glycosides and long chain α-1,4-glucosyl-derivatives (with up to nine α-1,4-glucosyl residues) was prepared (Sample 3).

Using a similar process as for sample 2, with exclusion of the aqueous alcohol treatment stage, a product containing high level non-modified glycosides, and short-chain derivatives (containing two or less α-1,4-glucosyl residues) was prepared (Sample 4). The composition of the samples is summarized in Table 1.

TABLE 1

Composition of glucosyl steviol glycosides samples

| Compounds | Content, % | | | |
|---|---|---|---|---|
| | Sample 1 | Sample 2 | Sample 3 | Sample 4 |
| Stevioside | 2.4 | 3.2 | 3.1 | 13.2 |
| Rebaudioside C | 0.7 | 1.0 | 1.0 | 3.0 |
| Rebaudioside A | 5.6 | 7.5 | 6.1 | 12.3 |
| Monoglucosyl-stevioside (StevG1) | 16.2 | 21.9 | 7.5 | 22.2 |
| Monoglucosyl-Rebaudioside A (RebAG1) | 20.9 | 28.1 | 11.2 | 22.4 |
| Diglucosyl-stevioside (StevG2) | 10.1 | 13.6 | 8.5 | 8.9 |
| Diglucosyl-Rebaudioside A (RebAG2) | 13.8 | 18.6 | 9.7 | 11.4 |
| Higher glucosylated derivatives | 1.3 | 1.7 | 48.8 | 1.8 |
| Total content of unreacted glycosides | 8.7 | 11.7 | 10.2 | 28.5 |
| Total content of glycosides | 71.0 | 95.5 | 95.8 | 95.3 |

The sensory assessment of samples was carried using aqueous solutions, with 20 panelists. Based on overall acceptance the most desirable and most undesirable samples were chosen. The results are shown in Table 2.

TABLE 2

Sensory assessment of samples in water system

| Judgment | Sample 1 | Sample 2 | Sample 3 | Sample 4 |
|---|---|---|---|---|
| Most desirable | 6 | 10 | 1 | 3 |
| Most undesirable | 1 | 0 | 12 | 7 |
| Sweetness power | 150 | 160 | 110 | 160 |
| Comments | Sweet, light, soft, round, pleasant, almost similar to sucrose, no lingering aftertaste, sweetness onset is rapid | Sweet, light, soft, round, pleasant, similar to sucrose, no lingering aftertaste, sweetness onset is rapid | Sweet, slightly bitter, astringent, slight lingering aftertaste, sweetness onset is moderate | Sweet, slightly bitter, astringent, slight lingering aftertaste, sweetness onset is slow |

As apparent from the results in Table 2, the sweetness quality of the Samples 1 and 2 was rated as most superior. Overall the samples with short-chain (containing two or less α-1,4-glucosyl residues) derivatives and low level of unreacted glycosides (Samples 1 and 2) possessed better taste profiles compared to samples with long-chain glucosyl derivatives (Sample 3) and short-chain (containing two or less α-1,4-glucosyl residues) derivatives and high level of unreacted glycosides (Sample 4).

Samples 1 and 2 show comparable sweetness power (150-160 times sweeter compared to a 5% sucrose solution) with control Sample 4 (160 times); however their flavor profile was clearly superior to the control Sample 4.

The compositions can be used as sweetness enhancers, flavor enhancers and sweeteners in various food and beverage products. Non-limiting examples of food and beverage products include carbonated soft drinks, ready to drink beverages, energy drinks, isotonic drinks, low-calorie drinks, zero-calorie drinks, sports drinks, teas, fruit and vegetable juices, juice drinks, dairy drinks, yoghurt drinks, alcohol beverages, powdered beverages, bakery products, cookies, biscuits, baking mixes, cereals, confectioneries, candies, toffees, chewing gum, dairy products, flavored milk, yoghurts, flavored yoghurts, cultured milk, soy sauce and other soy base products, salad dressings, mayonnaise, vinegar, frozen-desserts, meat products, fish-meat products, bottled and canned foods, tabletop sweeteners, fruits and vegetables.

Additionally the compositions can be used in drug or pharmaceutical preparations and cosmetics, including but not limited to toothpaste, mouthwash, cough syrup, chewable tablets, lozenges, vitamin preparations, and the like.

The compositions can be used "as-is" or in combination with other sweeteners, flavors and food ingredients.

Non-limiting examples of sweeteners include steviol glycosides, stevioside, Rebaudioside A, Rebaudioside B, Rebaudioside C, Rebaudioside D, Rebaudioside E, Rebaudioside F, dulcoside A, steviolbioside, rubusoside, as well as other steviol glycosides found in *Stevia rebaudiana* Bertoni plant and mixtures thereof, stevia extract, Luo Han Guo extract, mogrosides, high-fructose corn syrup, corn syrup, invert sugar, fructooligosaccharides, inulin, inulooligosaccharides, coupling sugar, maltooligosaccharides, maltodextins, corn syrup solids, glucose, maltose, sucrose, lactose, aspartame, saccharin, sucralose, sugar alcohols.

Non-limiting examples of flavors include lemon, orange, fruity, banana, grape, pear, pineapple, bitter almond, cola, cinnamon, sugar, cotton candy, vanilla flavors.

Non-limiting examples of other food ingredients include flavors, acidulants, organic and amino acids, coloring agents, bulking agents, modified starches, gums, texturizers, preservatives, antioxidants, emulsifiers, stabilisers, thickeners, gelling agents.

The following examples illustrate various embodiments of the invention. It will be understood that the invention is not limited to the materials, proportions, conditions and procedures set forth in the examples, which are only illustrative.

EXAMPLE 1

Preparation of CGTase

A strain of *Bacillus stearothermophilus* St-100 was inoculated in 2,000 liters of sterilized culture medium containing 1.0% starch, 0.25% corn extract, 0.5% $(NH_4)_2SO_4$, and 0.2% $CaCO_3$ (pH 7.0-7.5) at 56° C. for 24 hrs with continuous aeration (2,000 L/min) and agitation (150 rpm). The obtained culture broth was filtered using Kerasep 0.1 μm ceramic membrane (Novasep, France) to separate the cells. The cell-free permeate was further concentrated 2-fold on Persep 10 kDa ultrafilters (Orelis, France). The activity of the enzyme was determined according to Hale, Rawlins (1951). A crude enzyme preparation with activity of about 2 unit/mL was obtained.

EXAMPLE 2

Preparation of β-amylase

A strain of *Bacillus polymyxa* St-3504 was inoculated in 2,000 liters of sterilized culture medium containing 1.0% starch, 0.5% peptone, 0.5% corn extract, 0.5% NaCl, 0.02% $MnSO_4$ and 0.1% $CaCO_3$ (pH 7.0-7.5) at 32° C. for 24 hrs with continuous aeration (2,000 L/min) and agitation (150 rpm). The obtained culture broth was filtered using Kerasep 0.1 μm ceramic membrane (Novasep, France) to separate the cells. 10% of glucose was added to the cell-free permeate which was further concentrated on Persep 10 kDa ultrafilters (Orelis, France) and dried using Alpha 1-4 LSC freeze drier unit (Christ, Germany) to obtain a powder with 20,000 AUN/g activity. β-Amylase activity unit (1 AUN) was defined as the activity which liberates 100 μg of reducing sugar (expressed by dextrose equivalent) per minute under the following conditions: 1 mL of enzyme solution is mixed with 5 mL of 1.2% starch solution (pH 5.5, M/20 Acetate Buffer) and kept for 20 min at 40° C.

EXAMPLE 3

Preparation of Short-Chain Glucosyl *Stevia* Composition 100 g of tapioca starch was suspended in 300 mL of water (pH 6.5). 2 KNU of α-amylase (Termamyl Classic, Novozymes, Denmark) and 30 units of CGTase obtained according to EXAMPLE 1 were added, and the liquefaction of starch was carried out at 80° C. for about one hour to dextrose equivalent about 15. The pH of reaction mixture was adjusted to pH 2.8 by hydrochloric acid and the mixture was boiled at 100° C. during 5 minutes to inactivate the enzymes. After cooling to 65° C., the pH was adjusted to pH 6.0 with sodium hydroxide solution. 100 g stevia extract produced by PureCircle (JiangXi) Co., Ltd. (China), containing stevioside 29.2%, Rebaudioside A 54.3%, Rebaudioside C 9.0%, Rebaudioside F (1.7%) and other glycosides amounting to total steviol glycosides content of about 96.4% was added to liquefied starch and stirred until a homogeneous solution was obtained. 200 units of CGTase was added to the solution and the mixture was held at a temperature of 65° C. for 24 hours under continuous agitation. Then the temperature was reduced to 45° C., and 8,000 units of β-amylase obtained according to EXAMPLE 2 was added to reaction mixture. The reaction was continued for another 12 hours. The obtained reaction mixture was heated at 95° C. for 15 minutes to inactivate the enzymes. 20 grams of activated carbon was added and the mixture was heated to 75° C. and held for 30 minutes. The mixture was filtered and the filtrate was diluted with water to 5% solids content and passed through columns packed with Amberlite FPC23 (H$^+$) and Amberlite FPA51 (OH$^-$) ion exchange resins. The desalted solution was concentrated at 60° C. under vacuum, and dried into a powder form using laboratory spray dryer. The dried powder was suspended in 5 volumes of 95% aqueous ethanol. The suspension was agitated at 80° C., during 12 hours. Then the suspended solids were separated by filtration. The obtained solids were dried in vacuum dryer at 90° C. during 5 hours. 170 grams of product was obtained (Sample 1).

EXAMPLE 4

Preparation of Highly Purified Short-Chain Glucosyl *Stevia* Composition 100 g of tapioca starch was suspended in 300 mL of water (pH 6.5). 2 KNU of α-amylase (Termamyl Classic, Novozymes, Denmark) and 30 units of CGTase obtained according to EXAMPLE 1 were added, and the liquefaction of starch was carried out at 80° C. for about one hour to dextrose equivalent about 15. The pH of reaction mixture was adjusted to pH 2.8 by hydrochloric acid and the mixture was boiled at 100° C. during 5 minutes to inactivate the enzymes. After cooling to 65° C., the pH was adjusted to pH 6.0 with sodium hydroxide solution. 100 g stevia extract produced by PureCircle (JiangXi) Co., Ltd. (China), containing stevioside 29.2%, Rebaudioside A 54.3%, Rebaudioside C 9.0%, Rebaudioside F (1.7%) and other glycosides amounting to total steviol glycosides content of about 96.4% was added to liquefied starch and stirred until a homogeneous solution was obtained. 200 units of CGTase was added to the solution and the mixture was held at a temperature of 65° C. for 24 hours under continuous agitation. Then the temperature was reduced to 45° C., and 8,000 units of β-amylase obtained according to EXAMPLE 2 was added to reaction mixture. The reaction was continued for another 12 hours. The obtained reaction mixture was heated at 95° C. for 15 minutes to inactivate the enzymes. 20 grams of activated carbon was added and the mixture was heated to 75° C. and held for 30 minutes. The mixture was filtered and the filtrate was diluted with water to 5% solids content and passed through columns each packed with 4000 mL Amberlite XAD 7 HP macroporous adsorbent resin. The columns were washed with 5 volumes of water and 2 volumes of 20% (v/v) ethanol. The adsorbed glycosides were eluted with 50% ethanol. Obtained eluate was passed through columns packed with Amberlite FPC23 (H$^+$) and Amberlite FPA51 (OH$^-$) ion exchange resins. The ethanol was evaporated and the desalted and decolorized water solution was concentrated at 60° C. under vacuum, then dried into a powder form using laboratory spray dryer. The dried powder was suspended in 5 volumes of 95% aqueous ethanol. The suspension was agitated at 80° C., during 12 hours. Then the suspended solids were separated by filtration. The obtained solids were dried in vacuum dryer at 90° C. during 5 hours. 121 grams of product was obtained (Sample 2).

EXAMPLE 5

Preparation of Highly Purified Long-Chain Glucosyl *Stevia* Composition 100 g of tapioca starch was suspended in 300 mL of water (pH 6.5). 2 KNU of α-amylase (Termamyl Classic, Novozymes, Denmark) and 30 units of CGTase obtained according to EXAMPLE 1 were added, and the liquefaction of starch was carried out at 80° C. for about one hour to dextrose equivalent about 15. The pH of reaction mixture was adjusted to pH 2.8 by hydrochloric acid and the mixture was boiled at 100° C. during 5 minutes to inactivate the enzymes. After cooling to 65° C., the pH was adjusted to pH 6.0 with sodium hydroxide solution. 100 g stevia extract produced by PureCircle (JiangXi) Co., Ltd. (China), containing stevioside 29.2%, Rebaudioside A 54.3%, Rebaudioside C 9.0%, Rebaudioside F (1.7%) and other glycosides amounting to total steviol glycosides content of about 96.4% was added to liquefied starch and stirred until a homogeneous solution was obtained. 200 units of CGTase was added to the solution and the mixture was held at a temperature of 65° C. for 24 hours under continuous agitation. The obtained reaction mixture was heated at 95° C. for 15 minutes to inactivate the enzyme. 20 grams of activated carbon was added and the mixture was heated to 75° C. and held during 30 min. The mixture was filtered and the filtrate was diluted with water to 5% solids content and passed through columns each packed with 4000 mL Amberlite XAD 7 HP macroporous adsorbent resin. The columns were washed with 5 volumes of water and 2 volumes of 20% (v/v) ethanol. The adsorbed glycosides were eluted with 50% ethanol. Obtained eluate was passed through columns packed with Amberlite FPC23 (H$^+$) and Amberlite FPA51 (OH$^-$) ion exchange resins. The ethanol was evaporated and the desalted and decolorized water solution was concentrated at 60° C. under vacuum, then dried into a powder form using laboratory spray dryer. 165 grams of product was obtained (Sample 3).

EXAMPLE 6

Preparation of Highly Purified Short-Chain Glucosyl *Stevia* Composition 100 g of tapioca starch was suspended in 300 mL of water (pH 6.5). 2 KNU of α-amylase (Termamyl Classic, Novozymes, Denmark) and 30 units of CGTase obtained according to EXAMPLE 1 were added, and the liquefaction of starch was carried out at 80° C. for about one hour to dextrose equivalent about 15. The pH of reaction mixture was adjusted to pH 2.8 by hydrochloric acid and the mixture was boiled at 100° C. during 5 minutes to inactivate the enzymes. After cooling to 65° C., the pH was adjusted to pH 6.0 with sodium hydroxide solution. 100 g stevia extract produced by PureCircle (JiangXi) Co., Ltd. (China), containing stevioside 29.2%, Rebaudioside A 54.3%, Rebaudioside C 9.0%, Rebaudioside F (1.7%) and other glycosides amounting to total steviol glycosides content of about 96.4% was added to liquefied starch and stirred until a homogeneous solution was obtained. 200 units of CGTase was added to the solution and the mixture was held at a temperature of 65° C. for 24 hours under continuous agitation. Then the temperature was reduced to 45° C., and 8,000 units of β-amylase obtained according to EXAMPLE 2 was added to reaction mixture. The reaction was continued for another 12 hours. The obtained reaction mixture was heated at 95° C. for 15 minutes to inactivate the enzymes. 20 grams of activated carbon was added and the mixture was heated to 75° C. and held for 30 minutes. The mixture was filtered and the filtrate was diluted with water to 5% solids content and passed through columns each packed with 4000 mL Amberlite XAD 7 HP macroporous adsorbent resin. The columns were washed with 5 volumes of water and 2 volumes of 20% (v/v) ethanol. The adsorbed glycosides were eluted with 50% ethanol. Obtained eluate was passed through columns packed with Amberlite FPC23 ($H^+$) and Amberlite FPA51 ($OH^-$) ion exchange resins. The ethanol was evaporated and the desalted and decolorized water solution was concentrated at 60° C. under vacuum, then dried into a powder form using laboratory spray dryer. 154 grams of product was obtained (Sample 4).

EXAMPLE 7

Low-Calorie Orange Juice Drink

Orange concentrate (35%), citric acid (0.35%), ascorbic acid (0.05%), orange red color (0.01%), orange flavor (0.20%), Rebaudioside A (0.003%) and different glucosyl stevia compositions (0.03%) were blended and dissolved completely in water (up to 100%) and pasteurized. Glucosyl stevia compositions were represented by Samples 1, 2, 3 and 4, obtained according to EXAMPLES 3, 4, 5 and 6, respectively.

The sensory evaluations of the samples are summarized in Table 3. The data show that the best results can be obtained by using the high purity short-chain glucosyl stevia compositions (containing two or less α-1,4-glucosyl residues and low unreacted steviol glycosides) (Samples 1 and 2). Particularly the drinks prepared with Samples 1 and 2 exhibited a rounded and complete flavor profile and mouthfeel.

TABLE 3

Evaluation of orange juice drink samples

| Sample | Flavor | Aftertaste | Mouthfeel |
|---|---|---|---|
| No. 1 | High quality sweetness, pleasant taste similar to sucrose, rounded and balanced flavor | Clean, almost no bitterness, no aftertaste | Full |
| No. 2 | High quality sweetness, pleasant taste similar to sucrose, rounded and balanced flavor | Clean, no bitterness and no aftertaste | Full |
| No. 3 | High quality sweetness, pleasant taste almost similar to sucrose, rounded and balanced flavor | Clean, almost no bitterness, no aftertaste | Almost acceptable |
| No. 4 | Sweet, licorice notes | Slight bitterness and aftertaste | Not acceptable |

The same method can be used to prepare juices and juice drinks from other fruits, such as apples, lemons, apricots, cherries, pineapples, mangoes, etc.

EXAMPLE 8

Low-Calorie Carbonated Beverage

A carbonated beverage according to formula presented below was prepared.

| Ingredients | Quantity, % |
|---|---|
| Sucrose | 5.5 |
| Cola flavor | 0.340 |
| ortho-Phosphoric acid | 0.100 |
| Sodium citrate | 0.310 |
| Sodium benzoate | 0.018 |
| Citric acid | 0.018 |
| Rebaudioside A | 0.003 |
| Glucosyl stevia composition | 0.05 |
| Carbonated water | to 100 |

The sensory properties were evaluated by 20 panelists. The results are summarized in Table 4.

TABLE 4

Evaluation of low-calorie carbonated beverage samples

| | Number of panelists detected the attribute | | | |
|---|---|---|---|---|
| Taste attribute | Sample No. 1 | Sample No. 2 | Sample No. 3 | Sample No. 4 |
| Bitter taste | 0 | 0 | 10 | 12 |
| Astringent taste | 1 | 0 | 15 | 15 |
| Aftertaste | 1 | 0 | 13 | 18 |

TABLE 4-continued

Evaluation of low-calorie carbonated beverage samples

| Taste attribute | Number of panelists detected the attribute | | | |
|---|---|---|---|---|
| | Sample No. 1 | Sample No. 2 | Sample No. 3 | Sample No. 4 |
| | Comments | | | |
| Quality of sweet taste | Clean (18 of 20) | Clean (20 of 20) | Clean (14 of 20) | Bitter aftertaste (10 of 20) |
| Overall evaluation | Satisfactory (19 of 20) | Satisfactory (20 of 20) | Satisfactory (11 of 20) | Satisfactory (9 of 20) |

The above results show that the beverages prepared using Samples 1 and 2 possessed the best organoleptic characteristics.

EXAMPLE 9

Diet Cookies

Flour (50.0%), margarine (30.0%) fructose (10.0%), maltitol (8.0%), whole milk (1.0%), salt (0.2%), baking powder (0.15%), vanillin (0.1%) and different glucosyl stevia compositions (0.03%) were kneaded well in dough-mixing machine. The obtained dough was molded and baked in oven at 200° C. for 15 minutes. Glucosyl stevia compositions were represented by Samples 1, 2, 3 and 4, obtained according to EXAMPLES 3, 4, 5 and 6, respectively.

The sensory properties were evaluated by 20 panelists. The best results were obtained in samples prepared by high purity short-chain glucosyl stevia compositions (containing two or less α-1,4-glucosyl residues) derivatives (Samples 1 and 2). The panelists noted rounded and complete flavor profile and mouthfeel in cookies prepared with Samples 1 and 2.

EXAMPLE 10

Yoghurt

Different glucosyl stevia compositions (0.03%) and sucrose (4%) were dissolved in low fat milk. Glucosyl stevia compositions were represented by Samples 1, 2, 3 and 4, obtained according to EXAMPLES 3, 4, 5 and 6, respectively. After pasteurizing at 82° C. for 20 minutes, the milk was cooled to 37° C. A starter culture (3%) was added and the mixture was incubated at 37° C. for 6 hours then at 5° C. for 12 hours.

The sensory properties were evaluated by 20 panelists. The best results were obtained in samples prepared by high purity short-chain glucosyl stevia compositions (containing two or less α-1,4-glucosyl residues) derivatives (Samples 1 and 2). The panelists noted rounded and complete flavor profile and mouthfeel in samples prepared with Samples 1 and 2.

It is to be understood that the foregoing descriptions and specific embodiments shown herein are merely illustrative of the best mode of the invention and the principles thereof, and that modifications and additions may be easily made by those skilled in the art without departing for the spirit and scope of the invention, which is therefore understood to be limited only by the scope of the appended claims.

I claim:

1. A process for producing a highly purified glucosyl stevia composition, comprising the steps of:
    adding starch into water to form a starch suspension;
    adding a mixture of α-amylase and CGTase into the starch suspension and incubating for about 0.5 to 2 hours at about 75-80° C., resulting in a liquefied starch suspension;
    inactivating the α-amylase by low pH heat treatment;
    cooling the liquefied starch suspension and adjusting the pH to about 5.5 to 7.0;
    adding steviol glycosides into the liquefied starch suspension, resulting in a reaction mixture;
    adding a second batch of CGTase into the reaction mixture and incubating for about 12 to 48 hours at about 55-75° C.;
    adding a starch hydrolyzing enzyme to the reaction mixture and incubating for about 3-16 hours at about 40-60° C.;
    inactivating the enzymes in the reaction mixture by heat treatment;
    decolorizing the reaction mixture;
    removing non-diterpene compounds by contacting the decolorized reaction mixture with macroporous adsorbent resin and subsequently eluting adsorbed diterpene glycosides with aqueous ethanol to result in a glycoside-containing aqueous ethanol eluate;
    desalting the glycoside-containing aqueous ethanol eluate with ion-exchange resins;
    removing ethanol from the aqueous ethanol eluate, resulting in an aqueous eluate;
    concentrating and drying the aqueous eluate to obtain the dried glucosyl stevia composition,
    suspending the dried glucosyl stevia composition in aqueous alcohol to form a suspension, removing unmodified steviol glycosides from the suspension, and separating and drying the highly purified glucosyl stevia composition;
    wherein the highly purified glucosyl stevia composition comprises short-chain steviol glycoside derivatives having two or less α-1,4-glucosyl residues, and less than about 15% unmodified steviol glycosides.

2. The process according to claim 1, wherein the mixture of α-amylase and CGTase contains about 0.001-0.2 KNU of α-amylase per one unit of CGTase.

3. The process of claim 2, wherein the mixture of α-amylase and CGTase contains about 0.05-0.1 KNU of α-amylase per one unit of CGTase.

4. The process according to claim 1, wherein the weight of added steviol glycosides is about equal to that of the starch.

5. The process according to claim 1, wherein the added steviol glycosides are selected from the group consisting of stevioside, Rebaudioside A, Rebaudioside B, Rebaudioside C, Rebaudioside D, Rebaudioside E, Rebaudioside F, dulcoside A, steviolbioside, rubusoside, as well as other steviol glycosides found in *Stevia rebaudiana* Bertoni plant and mixtures thereof.

6. The process according to claim 1, wherein the CGTase is produced by cultures of *Bacillus stearothemophilus*.

7. The process according to claim 1, wherein the second batch of CGTase has about 0.2-4 units of CGTase per gram of solids.

8. The process according to claim 1, wherein the second batch of CGTase has about 0.5-1.2 units of CGTase per gram of solids.

9. The process according to claim 1, wherein after the hydrolyzing enzyme treatment, the short-chain glucosylated derivatives of stevioside and Rebaudioside A have two or less α-glucosyl residues.

10. The process of claim 1, wherein the oligo- or polysaccharide hydrolyzing enzyme is derived from one or more sources selected from the group consisting of animal, plant, bacterial and fungal sources.

11. The process according to claim 1, wherein the decolorizing is performed using activated carbon.

12. The process according to claim 1, wherein the decolorizing is performed using ion exchange resins or membranes, said membranes being selected from the group consisting of ultrafiltration, nanofiltration, and reverse osmosis membranes.

13. The process of claim 1, wherein removing non-diterpene compounds is conducted with a plurality of sequentially connected columns packed with a macroporous adsorbent resin, followed by washing the columns with water, then washing with about 10-50% (v/v) ethanol, disconnecting the columns, and then eluting each column individually with 30-100% ethanol.

14. The process according to claim 1, wherein the desalting is performed by passing the eluate through columns packed with ion exchange resins or membranes, said membranes being selected from the group consisting of ultrafiltration, nanofiltration, and reverse osmosis membranes.

15. The process according to claim 1, wherein the aqueous alcohol for suspending the dried glucosyl stevia composition comprises from about 0-50% (vol), water, and further comprising the steps of agitating the suspension at about 30-100° C., for a period of about 1-24 hours prior to separating the highly purified glucosyl stevia composition.

16. The process according to claim 1, wherein the highly purified glucosyl stevia composition has at least about 95% total steviol glycosides on an anhydrous basis.

17. The process according to claim 1, wherein the highly purified glucosyl stevia composition has less than 15% unreacted steviol glycosides on an anhydrous basis.

18. A sweetener composition comprising a highly purified glucosyl stevia composition made by the process of claim 1.

19. A flavor composition comprising a highly purified glucosyl stevia composition made by the process of claim 1.

20. A food ingredient comprising a highly purified glucosyl stevia composition made by the process of claim 1.

21. A food, beverage, cosmetic or pharmaceutical product comprising a highly purified glucosyl stevia composition made by the process of claim 1.

\* \* \* \* \*